(12) United States Patent
Bonanni et al.

(10) Patent No.: US 8,394,277 B2
(45) Date of Patent: Mar. 12, 2013

(54) REGENERATIVE PURIFICATION OF A PRETREATED BIOMASS STREAM

(75) Inventors: Andrea Bonanni, Rome (IT); Mariella Mule', Tortona (IT)

(73) Assignee: Beta Renewables, S.p.A., Tortona (AL) (IT)

( * ) Notice: Subject to any disclaimer, the term of this patent is extended or adjusted under 35 U.S.C. 154(b) by 0 days.

(21) Appl. No.: 13/503,042

(22) PCT Filed: Dec. 11, 2009

(86) PCT No.: PCT/IT2009/000562
§ 371 (c)(1),
(2), (4) Date: Apr. 20, 2012

(87) PCT Pub. No.: WO2011/070602
PCT Pub. Date: Jun. 16, 2011

(65) Prior Publication Data
US 2012/0211427 A1   Aug. 23, 2012

(51) Int. Cl.
*B01D 15/00* (2006.01)
*C01B 31/08* (2006.01)

(52) U.S. Cl. ........ 210/660; 502/416; 210/670; 210/372; 210/690; 210/694

(58) Field of Classification Search .................. 210/660, 210/670, 672, 690–694; 502/416
See application file for complete search history.

(56) References Cited

U.S. PATENT DOCUMENTS
2006/0065253 A1*   3/2006   Reddy ........................... 123/520

OTHER PUBLICATIONS

Rodrigues, R.C.L.B. et al., "The influence of pH, temperature and hydrolyzate concentration on the removal of volatile and nonvolatile compounds from sugarcane bagasse hemicellulosic hydrolyzate treated with activated charcoal before or after vacuum evaporation", Braz. J. Chem. Eng., Sep. 2001, vol. 18, No. 3.
Coelho, C et al., "The influence of activated carbon surface properties on the adsorption of the herbicide molinate and the bio-regeneration of the adsorbent", Journal of Hazardous Materials, Nov. 16, 2006, p. 343-349, vol. 138, No. 2, Elsevier, Amsterdam.
Ranjan, R et al., "Adsorption of fermentation inhibitors from lignocellulosic biomass hydrolyzates for improved ethanol yield and value-added product recovery", Microporous and Mesoporous Materials, Jun. 1, 2009, p. 143-148, vol. 122, No. 1-3, Elsevier Science Publishing, New York, U.S.
Lourdes A. Alves, Maria G.A. Felipe, Joao B. Almeida E. Silva, Silvio S. Silva and Arnaldo M.R. Prata, "Pretreatment of sugarcane bagasse hemicellulose hydrolysate for xylitol production by *Candida guilliermondii*", Applied Biochemistry and Biotechnology, Mar. 1, 1998, p. 89-98, vol. 70-72, No. 1.

* cited by examiner

*Primary Examiner* — Chester Barry
(74) *Attorney, Agent, or Firm* — Edwin A. Sisson, Attorney at Law, LLC

(57) ABSTRACT

It is disclosed a process for removing at least a portion of the furfural and acetic acid in a first stream comprised of water, at least one compound selected from the group consisting of furfural and acetic acid, C5's and C6's. Such process comprises the steps of contacting the stream with an adsorption media which has been previously contacted with a second stream comprised of the same components and the adsorption media has been regenerated by exposing it to conditions, without being in contact with the second stream, such that at least 70% of the adsorbed furfural and acetic acid have each been desorbed and at least 60% of the C5's and C6's remain adsorbed on the media.

13 Claims, No Drawings

REGENERATIVE PURIFICATION OF A PRETREATED BIOMASS STREAM

PRIORITY AND CROSS REFERENCES

This patent application claims the priority from PCT/IT2009/000562 (IT) filed 11 Dec. 2009.

FIELD

This specification is to the field of biomass for fermentation processes.

BACKGROUND

Preparation of a pre-treated biomass stream to benefit hydrolysis and subsequent fermentation are well known in the art. Taherzadeh and Karimi (2007) "Enzyme-based Ethanol", BioResources 2(4), 707-738 discuss the various pre-treament processes. In the pre treatment process, the biomass is treated with high pressure, high temperature steam or water and some water is removed. However, according to these authors, one of the goals is to avoid the formation of inhibitory by-products. However, rather than avoid formation, one could remove them. There exists therefore a need to economically remove the by-products of biomass pre-treatment.

SUMMARY

This specification discloses a process for removing at least a portion of the furfural and acetic acid in a first stream comprised of water, at least one compound selected from the group consisting of furfural and acetic acid, C5's and C6's, said process comprising the steps of contacting the stream with an adsorption media which has been previously contacted with a second stream comprised of the same components and the adsorption media has been regenerated by exposing it to conditions without being in contact with the second stream such that at least 70% of the adsorbed furfural and acetic acid have each been desorbed and at least 60% of the C5's and C6's remain adsorbed on the media. The first and second stream could be the same stream.

It is further disclosed that the regeneration is done raising the temperature of the media, which could be an activated carbon in a spherical shape, to a temperature at which the acetic acid and furfural will rapidly desorb and the C5's and C6's will slowly desorb for a time sufficient. It is disclosed that one can regenerate the media so that at least 80% of the adsorbed furfural and acetic acid have each been desorbed and at least 80% of the C5's and C6's remain adsorbed on the media. Reducing the pressure or vacuum is disclosed as one way to regenerate the media. An inert gas is also disclosed as a possible desorption condition.

It is also disclosed that the removal could be preceded by a concentration step which removes at least 20% by weight of the water in the first stream and that the removal step or concentration step could be preceded by a solids removal step to remove at least a portion of the solids from the first stream. It is also disclosed that the stream may be diluted with water before further processing.

Also disclosed is an article of manufacture comprised of an adsorption media which has been made contacting the adsorption media with a stream comprised of water, C5's, C6's, furfural and acetic acid for sufficient time that the amount of the C5's and the C6's adsorbed onto the media are at least 90% of the maximum level of the C5's and the C6's that can be respectively adsorbed onto the media and the media regenerated so that the that the amount of C5's and C6's on the media are at least 80% of the maximum level of the C5's and the C6's that can be respectively adsorbed onto the media.

DESCRIPTION

The process acts upon a pretreated biomass in a pretreated biomass stream.

The pretreated biomass is comprised of a liquid stream having a dry content expressed in terms of soluble and dissolved solids plus water and with the presence of organic compounds like sugars and organic acids.

The pre-treated biomass can be characterized on the basis of its water, C5, C6, acetic acid, formic acid and furfural. The total C5's of the composition is the sum of arabinan and xylan in the composition which includes the monomers, dimers, oligomers and polymers of arabinose and xylose in the liquid and solid of the composition. The total C6's in the composition is the glucan content which includes the monomers, dimers, oligomers and polymers of glucose that may be present in the liquid and solids of the streams.

The pretreated biomass usually comes from a lignocellulosic biomass or lignocellulosic compounds which has been pretreated by means of a process where the biomass, chosen as a preferred feedstock that is usually a plant biomass with cellulose, hemicelluloses and lignin, is added with water or steam or chemicals or a combination of these and maintained for a certain time at a certain temperature to obtain the pretreated biomass with a dry content and a water portion.

The water is usually present in the form of water absorbed into the biomass itself and in the form of free water. The term biomass and water means the dry content of the biomass plus all the water which includes the water present prior to pretreatment and the adsorbed water and the free water which have been added during the pretreatment process.

The pretreated biomass stream is usually sent to a separation step where the pretreated liquid biomass stream is often separated in a liquid form by a separation step using filters, press or membrane or any other procedure able to separate and collect a liquid stream with a dry solid composed of soluble plus dissolved solids plus water. This is an example of a pretreated biomass liquid stream.

The pretreated biomass stream and the pretreated biomass liquid stream contain some compounds that are hydrolysable into water soluble species from the hydrolysis of the dry portion of biomass.

Glucose and xylose are examples of hydrolyzed compounds.

During the pretreatment step other organic compounds are usually formed or extracted from the biomass. These compounds usually derive from the cellulose or from the hemicellulose or from the lignin portions. In some cases other organic compounds are present in the pretreated biomass stream due to organic compounds like starch or extractives in the inlet biomass feedstock to the pretreated process. These organic compounds, such as furfural, formic acid, and acetic acid, or at least a portion of them can be separated and collected in the pretreated biomass liquid stream.

The process described below has been able to remove one or more organic compounds of interest like the acetic acid from the pretreated liquid biomass stream by using an adsorbent media. The process minimizes the total amount of adsorbent media needed to reach the desired level of organic compound of interest and minimize total loss of sugars or oligomers or polymers like glucose and xylose.

In addition to adsorbing the organics impurities of furfural and acetic acid, the selected adsorbent media can be regenerated so as to remove the impurities yet keep the adsorbed C5's and C6's on the media so that in the second, and subsequent uses, only the impurities are absorbed, or at least a small fraction of the C5's and C6's are adsorbed.

The adsorbent media can be an activated carbon or a high surface polymer, such as polystyrene with activated carbon. These polymeric mediums are available from Blücher G.m.b.H, Germany under the tradename SARATECH®. The manufacture of these high surface area polymeric spherical activated carbon particles is described in US 20060148645 and US 2008171648.

While the process disclosed below comprises a concentration step, an adsorption step, and a regeneration step, with option filtration, the process exists without the concentration step.

The concentration step is to remove as much water was economically possible, knowing that many of the non-C5 and non-C6's will be removed. The concentration step can be performed with already existing techniques and likely some which have yet been invented. Typical concentrating techniques include but are not limited to those selected from the group consisting of evaporators, vacuums, flash distillations, distillations, centrifuges, cyclones and hydrocylones.

The minimum value of concentration of the organic compounds of interest, like the acetic acid or furfural, is the concentration at which a discrete increase of concentration of the same organic component does not change the adsorption capability of the adsorbent media to adsorb the organic compound of interest from the liquid pretreated biomass stream in a significant way. The minimum value of concentration is usually expressed in terms of quantity of organic material in the solution and expressed another way is the concentration that the compound of interest should have after the adsorption step.

The process is very specific since it depends upon the organic compound of interest, upon the temperature and upon the concentration of the organic compound of interest to be removed from the liquid pretreated biomass stream.

The minimum concentration value of the organic compound of interest can be measured by adding a small discrete quantity of the same organic compound and measuring the delta increase of adsorbent capability of the adsorbent media as regards with the organic compound of interest.

The preferred process condition is the condition at which an addition of a small quantity of the organic compound of interest does not change significantly the capability of the adsorbent media of adsorbing the organic compound of interest per unit of time and per unit of adsorbent media and at the same constant temperature.

After the concentration step, the concentration of the organic compound of interest in the liquid pretreated biomass stream after the concentration step should be equal to or higher than the minimum concentration of the organic component of interest in the liquid pretreated biomass stream in order to maximize the adsorbent capability of the adsorbent media during the adsorbing process.

When the concentration of the organic compound of interest is such that a small increase of the organic compound of interest in the liquid pretreated biomass stream changes the adsorbent capability of the media to adsorb the organic compound of interest in a way that is higher than a small delta of adsorbent capability, the concentration process will concentrate the pretreated biomass stream at a concentration level of the organic compound of interest higher than the minimum concentration of the organic compound of interest at which an increase of concentration of the organic compound of interest does not change the adsorbent capability of the media to adsorb the organic compound of interest in a way that is higher than the same small delta.

As shown in the experiment using a 9 Liter sample, 3 Liter was removed by roto-evaporation.

After the concentration step, the concentrated pretreated liquid biomass stream is subjected to an adsorbent process where the composition is contacted with at least one adsorption media to remove at least some of the organic impurities of interest.

The adsorbent media is selected according to its ability to be regenerated. What has been learned is that the adsorbent media will adsorb the organic impurities as well as a portion of the C5's and C6's. Thus if one were to use the media once, one would remove the impurities as well as a portion of the product of interest. While one could regenerate the adsorbent media, the regenerated media would still adsorb the C5's and C6's. However, it has been discovered that at least some media, when regenerated, will keep the C5's and C6's adsorbed to the media. When the regenerated media with the C5's and C6's still adsorbed is reused, the regenerated media will remove the impurities from the solution, but will remove very little of the C5's/C6's from the solution, if any at all.

Regeneration of the adsorbent media is usually done with industry techniques. In the examples below, the media was heated and the volatiles de-sorbed. The media could be heated under vacuum, heated with steam or hot water, or other hot stream that strip the organic compound of interest more than the C5's and C6's.

The regeneration step is usually performed by increasing the temperature of the media. A pressure change of the pressure condition of the media or the use of a heat stream like hot water or steam or other compound able to desorb the organic compounds of interest passed through the media can be also used to regenerate the media itself.

The regeneration can comprise the conditions of or consisting of or consisting essentially of maintaining the temperature, pressure and time or the other variable used to regenerate the media at a level higher than the value at which the organic compound of interest starts to be desorbed and lower than the value at which the sugar or the oligomer or the polymer tends to be desorbed.

The regeneration step will be done at these conditions so that at least 50% by weight of the C5/C6's remain with the media and more than at least 80% or 90% by weight of the non-C5 and non-C6 organics are removed from the media. Even more preferred is that at least 75% by weight of the C5/C6's remain with the media, with more than at least 90% by weight of the C5/C6's remaining with the media being the most preferred. The C5/C6 value is not linked to the removal of the non-C5 and non-C6s removed from the media.

For example, while it is preferred that at least 50% by weight of the total amount of C5's and C6's remain with the media, it is more preferred that at least 60% by weight of the total amount of C5's and C6's remain with the media, with it being more preferred that at least 70% by weight of the total amount of C5's and C6's remain with the media, with it being even more preferred that at least 80% by weight of the total amount of C5's and C6's remain with the media, with it being most preferred that at least 90% by weight of the total amount of C5's and C6's remain with the media.

For the non-C5 and non-C6's at least 50% by weight of the total amount of non-C5's and non-C6's are removed from the media, it is more preferred that at least 60% by weight of the total amount of non-C5's and non-C6's are removed from the media, with it being more preferred that at least 70% by weight of the total amount of non-C5's and non-C6's are removed from the media, with it being even more preferred that at least 80% by weight of the total amount of non-C5's and non-C6's are removed from the media, with it being most preferred that at least 90% by weight of the total amount of non-C5's and non-C6's are removed from the media.

In the interest of specificity, in the case of furfural at least 50% by weight of the total amount of the furfural is removed from the media, it is more preferred that at least 60% by weight of the total amount of the furfural is removed from the media, with it being more preferred that at least 70% by weight of the total amount of the furfural is removed from the media, with it being even more preferred that at least 80% by weight of the total amount of the furfural is removed from the media, with it being most preferred that at least 90% by weight of the total amount of the furfural removed from the media.

In the case of acetic acid at least 50% by weight of the total amount of the acetic acid is removed from the media, it is more preferred that at least 60% by weight of the total amount of the acetic acid is removed from the media, with it being more preferred that at least 70% by weight of the total amount of the acetic acid is removed from the media, with it being even more preferred that at least 80% by weight of the total amount of the acetic acid is removed from the media, with it being most preferred that at least 90% by weight of the total amount of the acetic acid removed from the media.

This step permits to recover the capability of adsorbing the organic compound of interest of the adsorbent media and to minimize the amount of sugar that will be adsorbed when the media is used again after the regeneration step. After regeneration, the regenerated media is used again to purify more pretreated liquid biomass stream.

After the adsorption step, the purified liquid biomass stream can be further processed.

Because the pretreated liquid biomass stream will have some solids, it may be preferable to separate the solids from the stream before concentration, but most particularly prior to contacting the adsorption media.

EXPERIMENTAL

Tables 1 and 2 below establish the value of regeneration. In Table 1, a stream containing glucose and xylose at 1.385 and 3.01 g/dm$^3$ respectively, were passed over the amount of spherical media obtained from Blucher. The amount of media used in grams per liter of stream and the exposure time are indicated. The amount of C5's and C6's remaining in the solution and percent adsorbed are indicated. The data in Table 1 are for the fresh media indicating a high loss of xylose.

TABLE 1

FRESH MEDIA, NO REGENERATION

| MEDIA | | | GLUCOSE | | XYLOSE | |
|---|---|---|---|---|---|---|
| | | | | % Absorbed | | % Absorbed |
| | | | Amount in | (removed) | Amount in | (removed) |
| Amount (g/l) | Time (min) | Liquid (g/dm$^3$) | per 100 g media | | Liquid | per 100 g media |
| 100 | 2 | 1.183 | 14.6 | | 2.277 | 24.4 |
| 100 | 7 | 1.046 | 24.5 | | 1.882 | 37.5 |
| 100 | 12 | 0.835 | 39.7 | | 1.383 | 54.1 |
| 200 | 2 | 0.902 | 17.4 | | 1.557 | 24.1 |
| 200 | 7 | 0.715 | 24.2 | | 1.124 | 31.3 |
| 200 | 12 | 0.613 | 27.8 | | 0.893 | 35.2 |

TABLE 1-continued

FRESH MEDIA, NO REGENERATION

| MEDIA | | | GLUCOSE | | XYLOSE | |
|---|---|---|---|---|---|---|
| | | | | % Absorbed | | % Absorbed |
| | | | Amount in | (removed) | Amount in | (removed) |
| Amount (g/l) | Time (min) | Liquid (g/dm$^3$) | per 100 g media | | Liquid | per 100 g media |
| 50 | 2 | 1.415 | −4.33 | | 2.664 | 23.0 |
| 50 | 7 | 1.312 | 10.54 | | 2.443 | 37.8 |
| 50 | 12 | 1.221 | 23.7 | | 2.206 | 53.4 |

In Table 2, a stream containing the same glucose and xylose concentrations at 1.385 and 3.01 g/dm$^3$ respectively, were passed over the same media as in Table 1. The amount of media used in grams per liter of stream and the exposure time are indicated. The amount of C5's and C6's remaining in the solution and percent adsorbed are indicated. However, in this instance, the media had been used once and then regenerated by exposing it to 150° C. for 20 minutes. The regenerated media were capable of adsorbing more of the organic impurities, but as can be seen, the maximum loss was 7% per 100 g media for xylose, or 20% the loss of fresh media.

TABLE 2

MEDIA, AFTER REGENERATION

| MEDIA | | | GLUCOSE | | XYLOSE | |
|---|---|---|---|---|---|---|
| | | | | % Absorbed | | % Absorbed |
| | | | Amount in | (removed) | Amount in | (removed) |
| Amount (g/l) | Time (min) | Liquid (g/dm$^3$) | per 100 g media | | Liquid | per 100 g media |
| 100 | 2 | 1.437 | −3.8 | | 3.04 | −1.0 |
| 100 | 7 | 1.427 | −3.0 | | 2.924 | 2.9 |
| 100 | 12 | 1.381 | 0.3 | | 2.902 | 3.6 |
| 200 | 2 | 1.444 | −2.1 | | 2.895 | 1.9 |
| 200 | 7 | 1.364 | 0.8 | | 2.78 | 3.8 |
| 200 | 12 | 1.286 | 3.6 | | 2.598 | 6.8 |
| 50 | 2 | 1.448 | −4.5 | | 3.027 | −0.6 |
| 50 | 7 | 1.396 | −0.8 | | 2.905 | 3.5 |
| 50 | 12 | 1.409 | −1.7 | | 2.891 | 4.0 |

The negative values indicate that some of the sugars desorbed into the solution.

Table 3 demonstrates the ability to the process to remove the contaminants. The solution was concentrated by vaporization for 1.5 hr at 55 C in multiple steps. In each step 1.5 l was reduced to 1.0 l, corresponding with 33% volume reduction. The concentrated solution was treated in a stirred beaker containing 100 g/l solution of adsorbent media SARATECH® mircroporous type (same media as in Tables 1 and 2) for 10 minutes. The solution was rediluted with demineralized water to take the analysis so that the concentrations and losses could be made on a comparable basis.

TABLE 3

REMOVAL AT EACH STEP

| ID | Start Sol'n g/L | After Conc. of 33% wt Removal g/L | Removal through evap % of starting amount | After treatment with Bluecher resins in batch mode for 10 min g/L | Solution after treatment with Bluecher resins in batch mode for 10 min g/L | Adsorb Removal Yield: % of concentrated Amount | Total Removal yield: adsorb + evap % of starting amount |
|---|---|---|---|---|---|---|---|
| Glucose | 1.524 | 2.255 | −1.5% | 1.75 | 1.1655 | −22% | −23.5% |
| Xylose glicerol | 3.1388 | 4.571 | −3.0% | 3.319 | 2.210454 | −27% | −29.6% |
| Formic Acid | 0.856 | 1.287 | 0.1% | 0.977 | 0.650682 | −24% | −24.0% |
| Acetic Acid | 4.923 | 6.645 | −10.1% | 2.7 | 1.7982 | −59% | −63.5% |
| 5 HMF | 0.315 | 0.472 | −0.2% | 0.00022 | 0.000147 | −100% | −100.0% |
| 2-Furfural | 0.0915 | 0.0033 | −97.6% | | 0.000 | −100% | −100.0% |
| Liquid vol. | 1 liter | 10 | | 10 | | | |
| Dry mass | | 0.8201 | | | 0.7711 | | |

We claim:

1. A process for removing at least a portion of the furfural and acetic acid in a first stream comprised of water, C5's, C6's, and at least one compound selected from the group consisting of acetic acid and furfural, said process comprising the steps of contacting the stream with an adsorption media which has been previously contacted with a second stream comprised of the same components and the adsorption media has been regenerated by exposing it without being in contact with the second stream to conditions such that at least 70% of the adsorbed furfural and acetic acid have each been desorbed and at least 60% of the C5's and C6's remain adsorbed on the media, wherein said media is an activated carbon or a high surface polymer.

2. The process according to claim 1, wherein the first and second stream are the same stream.

3. The process according to claim 1, wherein the exposure for regeneration is done by raising the temperature of the media to a temperature at which the acetic acid and furfural will rapidly desorb and the C5's and C6's will slowly desorb for a time sufficient so that at least 80% of the adsorbed furfural and acetic acid have each been desorbed and at least 80% of the C5's and C6's remain adsorbed on the media.

4. The process according to claim 1, wherein the exposure for regeneration is done by reducing the pressure.

5. The process according to claim 1, wherein the removal step is preceded by a concentration step which removes at least 20% by weight of the water in the first stream.

6. The process according to claim 1, wherein each step is preceded by a solids removal step to remove at least a portion of the solids from the first stream.

7. The process according to claim 1, wherein the regeneration uses an inert gas in contact with the adsorption media.

8. The process according to claim 1, wherein the purified liquid biomass stream is diluted with water before further processing.

9. The process according to claim 1, wherein the adsorption media comprises a spherical polymeric media with active carbon.

10. A process for regenerating an adsorption media which is an activated carbon or a high surface polymer by contacting the adsorption media with a stream comprised of water, C5's, C6's, furfural and acetic acid for sufficient time so that the amount of the C5's and the C6's adsorbed onto the media are at least 90% of the maximum level of the C5's and the C6's that can be respectively adsorbed onto the media and by subsequently regenerating the media so that the amount of C5's and C6's on the media are at least 76% of the maximum level of the C5's and the C6's that can be respectively adsorbed onto the media, and at least 50% by weight of the total amount of the furfural and acetic acid, respectively, is removed from the media.

11. The process of claim 10, wherein the amount of C5' and C6's on the media is at least 84% of the maximum level of the C5's and the C6's that can be respectively adsorbed onto the media.

12. The process of claim 10, wherein the amount of C5' and C6's on the media is at least 90% of the maximum level of the C5's and the C6's that can be respectively adsorbed onto the media.

13. The process of claim 10, wherein the amount of C5' and C6's on the media is at least 95% of the maximum level of the C5's and the C6's that can be respectively adsorbed onto the media.

* * * * *